(12) United States Patent
Cady

(10) Patent No.: US 12,262,766 B2
(45) Date of Patent: Apr. 1, 2025

(54) PROTECTIVE VEST DEVICE AND RELATED METHOD THEREOF

(71) Applicant: University of Virginia Patent Foundation, Charlottesville, VA (US)

(72) Inventor: Patricia A. Cady, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 559 days.

(21) Appl. No.: 17/607,931

(22) PCT Filed: May 1, 2020

(86) PCT No.: PCT/US2020/031015
§ 371 (c)(1),
(2) Date: Nov. 1, 2021

(87) PCT Pub. No.: WO2020/223627
PCT Pub. Date: Nov. 5, 2020

(65) Prior Publication Data
US 2022/0304406 A1    Sep. 29, 2022

Related U.S. Application Data

(60) Provisional application No. 62/842,104, filed on May 2, 2019.

(51) Int. Cl.
*A61F 5/00* (2006.01)
*A41B 13/06* (2006.01)
(Continued)

(52) U.S. Cl.
CPC .......... *A41D 13/1272* (2013.01); *A41B 13/06* (2013.01); *A61F 5/3746* (2013.01); *A61J 15/0053* (2013.01)

(58) Field of Classification Search
CPC ...... A47D 15/005; A47D 15/00; A47D 15/04; A61F 5/0118; A61F 5/05858;
(Continued)

(56) References Cited

U.S. PATENT DOCUMENTS

| 1,678,125 A | * | 7/1928 | Petrescu | ................ A41B 13/06 5/413 R |
| 3,315,671 A | | 4/1967 | Creelman | |

(Continued)

OTHER PUBLICATIONS

Da Silva PS, et al., "Unplanned extubation in the neonatal ICU: A systematic review, critical appraisal, and evidence-based recommendations", Respiratory Care, Jul. 2013, vol. 58, No. 7, pp. 1237-1245, doi: 10.4187/respcare.02164.
(Continued)

*Primary Examiner* — Adam Baker
(74) *Attorney, Agent, or Firm* — Robert J. Decker

(57) ABSTRACT

A protective vest device that will adequately secure an infant from the ability to self-dislodge medical life-sustaining supply lines or equipment, while also supporting proper body alignment. The protective device mitigates self-dislodgement while allowing for free movement and proper alignment of infant's arms and hands and which are allowed to touch one another, thereby not inhibiting the ability to explore and expand brain development through tactile stimulation and therefore fostering healthy neuronal pathways of the infant. The fostering healthy neuronal pathways is provided by, for example, allowing the hands to touch one another as the infant develops a sense of where it is in space and time as it continues to grow outside of the womb. By maintaining proper body alignment of infant in the device and the configuration of the device, the device supports healthy musculoskeletal development with a stretchy womb like material to mimic the spring back effect of the uterine wall when a fetus pushes against a uterus.

23 Claims, 9 Drawing Sheets

(51) Int. Cl.
*A41D 13/12* (2006.01)
*A61F 5/37* (2006.01)
*A61J 15/00* (2006.01)

(58) Field of Classification Search
CPC ...... A61F 5/3723; A61F 5/373; A61F 5/3738; A61F 5/3746; A61F 5/3753; A61F 5/3715; A61F 5/3756; A41B 13/005; A41B 13/00; A41B 13/10; A41B 13/103; A41B 13/06; A41B 13/065; A41D 13/1272; A41D 13/02; A47G 9/083
USPC .......................................................... 128/874
See application file for complete search history.

(56) References Cited

U.S. PATENT DOCUMENTS

| | | | |
|---|---|---|---|
| 4,688,270 | A | 8/1987 | Denicola et al. |
| 5,425,381 | A | 6/1995 | Peterson et al. |
| 7,882,570 | B2 | 2/2011 | Krier |
| 8,782,831 | B2 | 7/2014 | Houston et al. |
| 9,332,791 | B1 * | 5/2016 | Bush .............. A47D 15/003 |
| 9,474,669 | B1 | 10/2016 | Bush et al. |
| 9,820,907 | B1 | 11/2017 | Bush et al. |
| 2010/0071709 | A1 * | 3/2010 | Grissom ............... A41B 13/06 128/870 |
| 2010/0275373 | A1 * | 11/2010 | Kaplan ................ A41B 13/06 5/494 |
| 2011/0083276 | A1 * | 4/2011 | Pieta ..................... A41B 13/06 5/655 |
| 2016/0295928 | A1 * | 10/2016 | Bopanna ............... A41B 13/06 |
| 2017/0055591 | A1 | 3/2017 | Clouse et al. |
| 2017/0212192 | A1 | 7/2017 | Rapoport et al. |

OTHER PUBLICATIONS

Dalgleish, Stacey, et al., "Special considerations in neonatal mechanical ventilation", Critical Care Nursing Clinics, 2016, vol. 28, No. 4, pp. 477-498, doi: S0899-5885(16)30056-9.
Panagos, Patoula G. et al., "Creating a highly reliable neonatal intensive care unit through safer systems of care" Clinics in Perinatology, 2017, vol. 44, No. 3, pp. 645-662.
Powell, Bonnie M., et al., "Reducing unplanned extubations in the NICU using lean methodology", Respiratory Care, Dec. 2016, vol. 61, No. 12, pp. 1567-1572, doi: 10.4187/respcare.04540.
Merkel, Lori, et al., "Reducing unplanned extubations in the NICU", Pediatrics, May 2014, vol. 133, No. 5, pp. e1367-e1372, doi:10.1542/peds.2013-3334.
Barber, Jessica A, "Unplanned extubation in the NICU", Journal of Obstetric, Gynecologic & Neonatal Nursing, 2013, vol. 42, No. 2, pp. 233-238.
Kurachek, Stephen C., et al., "Extubation failure in pediatric intensive care: a multiple-center study of risk factors and outcomes", Critical Care Medicine, 2003, vol. 31, No. 11, pp. 2657-2664.
Muraskas, Jonathan, "The cost of saving the tiniest lives: NICUs versus prevention", Virtual Mentor, Oct. 2008; vol. 10, No. 10, pp. 655-658.
Society of Critical Care Medicine, "Critical Care Statistics", obtained from https://www.sccm.org/Communications/Critical-Care-Statistics, extracted on Sep. 26, 2024, 11 pages.
Hatch, L. Dupree, et al., "Effect of anatomical and developmental factors on the risk of unplanned extubation in critically ill newborns", American journal of perinatology, Oct. 2017, vol. 34, No. 12, pp. 1234-1240.
Mbi Ndakor, S. et al., "Counting unplanned extubations: marked variation among neonatologists", Journal of Perinatology, 2017, (published online Feb. 2, 2017) vol. 37, No. 6, pp. 698-701.
WIPO, "International Search Report and Written Opinion of the International Searching Authority", International patent application No. PCT/US2020/031015, mailed Jul. 15, 2020, 8 pages.

* cited by examiner

PROTECTIVE VEST DEVICE AND RELATED METHOD THEREOF

RELATED APPLICATIONS

The present application is a national stage filing of International Application No. PCT/US2020/031015, filed May 1, 2020, which claims benefit of priority under 35 U.S.C § 119 (e) from U.S. Provisional Application Ser. No. 62/842,104, filed May 2, 2019, entitled "Ventilator Vest Device and Related Method Thereof": the disclosures of which are hereby incorporated by reference herein in their entirety.

FIELD OF INVENTION

The present disclosure relates generally to a protective vest device that will adequately secure an infant from the ability to self-dislodge medical life-sustaining supply lines or equipment, while also supporting proper body, hands, and arms alignment. More particularly, while mitigating self-dislodgement, the protective device allows for free movement and proper alignment of infant's arms and hands and which are allowed to touch one another, thereby not inhibiting the ability to explore and expand brain development through tactile stimulation and therefore fostering healthy neuronal pathways of the infant.

BACKGROUND

Unplanned extubations (UEs) are the fourth leading cause of adverse events in NICUs across the country [See 1-5]. The action of re-intubating infants, in an unplanned and stressful environment, subjects them to increased risk of developing ventilator-associated pneumonia, airway trauma, subglottic stenosis [See 2, 3, 5, 6], chronic lung disease [See 1, 2, 5] and intraventricular hemorrhage (IVH) [See 1, 5]. Dalgleish et al. [See 2] also points out that UEs cause an increase in overall ventilator days for affected patients. As these infants develop, they are adversely affected on a long-term basis. IVH leads to developmental delays, or even cerebral palsy, while chronic lung disease predisposes infants to prolonged invasive ventilation, such as the eventual need for a tracheostomy.

Silva et al. [See 1] conducted a systematic review of the literature from around the world, from 1950 through 2012, and concluded that the rate of UEs continue to remain the same, when compared to the last five years. Little, to no, progress has been made in protecting the airways of the smallest patients around the world. Here in America, national standards have been set for both the pediatric and adult world of medicine as regards the rate of UEs, yet none formally exist for neonates [See 4]. In 2012, the Vermont Oxford Network established a suggestion of no more than two UEs per 100 ventilator days for neonates [See 5]. Merkel et al. [See 5] suggests there is no reason why NICUs nationwide should not be adopting the mindset that UEs become a "Never Event". An aspect of an embodiment of the present invention ventilator vest device not only strives toward such a goal but substantially achieves toward such a goal as well as various other goals.

Current swaddle products on the market fail to completely contain the patient's arms. Based on clinical bedside expertise, infants have the ability to wriggle their way out of containment attempts.

An aspect of an embodiment of the present invention provides, among other things, an environment in which infants have the ability to feel their own hands and maintain proper upper-body, and in midline alignment, whereby the developmental processes of the infant are fostered and supported. The safe movement of the hands and arms ensures that the integrity of the endotracheal tube (ETT) (or other medical supply line or equipment) is well guarded from self-extubation (or other types of self-dislodgement).

An aspect of an embodiment of the present invention provides, among other things, a swaddle device (and ventilator vest device or protective vest device) that is only as long as the length of the rib cage, and wherein any umbilical lines will be continuously visible by the medical team, including hourly depth affirmation performed by the bedside registered nurse (RN). In an embodiment, the use of Velcro (or other attachment mechanisms, materials, and means) will allow easy access for the hourly visualization of any intravenous (IV) lines on the hands or arms. In an embodiment, appropriately positioned small openings on each side of the device will allow IV lines to exit the device without infringement.

Hatch, et al. [See 13] reports the incidence of self-extubation rates in their facility as high as forty percent, while Ndakor, Nelson, and Pinheiro [See 14] reported that the 310 NICU neonatologists who tracked the incidence of UEs in their own facilities, indicated the accidental removal of the ETT by the patient, to be as high as sixty-five percent.

Due to the status that most often, intubated neonates are not sedated, this places them at increased risk for unplanned extubations (UE), and so there is a need to mitigate unplanned extubations (UE).

The market currently lacks any device which will adequately secure an infant from the ability to self-extubate, while also supporting proper body alignment.

The market currently lacks any device that while mitigating unplanned extubations (UE), will also advantageously contain the arms and hands of neonates, as well as also supply a form of natural soothing, and thus decreasing the need for sedation in vulnerable developing brains.

The market currently lacks any device that while mitigating unplanned extubations (UE), the infant's hands will remain contained and enclosed, while allowing free movement and proper alignment of their hands and arms.

The market currently lacks any device, that while mitigating unplanned extubations (UE), provides an environment in which the arms and hands are allowed to touch one another, thereby not inhibiting the ability to explore and expand brain development through tactile stimulation.

There is a need in the art for unnecessarily overly restricting the infant's hands and/or arms while also preventing self-dislodgements.

SUMMARY OF EXEMPLARY EMBODIMENTS OF THE PRESENT INVENTION

An aspect of an embodiment of the present invention provides, among other things, a protective vest device for preventing a self-dislodgement by an infant of medical life-sustaining (or non-life-sustaining) supply lines or equipment while allowing free movement and proper alignment of an infant's hands and arms. The device may comprise: a supine portion for receiving the torso of the infant in a supine position: a lateral portion, wherein the lateral portion is configured to fold over the torso of the infant without covering the hands and arms of infant to wrap around at least the anterior portion of the torso, and disposed posterior to the hands specified in a cross-hands position across the chest of the infant; and a protective portion including a support portion, wherein the protective portion is configured to fold over and enclose at least the anterior portion of the torso, hands and arms of the infant, and wherein the support portions provide supportive force in the anterior direction of the folded and enclosed protective portion to provide separation of the folded and enclosed protective portion away from the hands and arms while the hands are in a specified crossed-hands position on the torso, across the chest of the infant. Moreover, the separation of the folded and enclosed protective portion provides clearance to allow the hands and arms to move in the posterior-anterior direction, lateral-medial direction, and superior-inferior direction relative to the chest of the torso. Further, wherein: by allowing for the free movement and proper alignment of infant's arms and hands and which are allowed to touch one another, thereby not inhibiting the ability to explore and expand brain development through tactile stimulation and therefore fostering healthy neuronal pathways of the infant as the infant develops a sense of where it is in space and time as it continues to grow outside of the womb. Further yet, the folded and enclosed protective portion prevents the arms and hands traveling beyond the enclosed protective portion thereby preventing any self-dislodgement by the infant of the medical life-sustaining supply lines or equipment.

An aspect of an embodiment of the present invention provides, among other things, a method for preventing a self-dislodgement by an infant of medical life-sustaining (or non-life-sustaining) supply lines or equipment while allowing free movement and proper alignment of an infant's hands and arms. The method may comprise: receiving the torso of the infant in a supine position on a supine portion of a vest device: folding a lateral portion of the vest device over the torso of the infant without covering the hands and arms of infant to wrap around at least the anterior portion of the torso, and disposing the lateral portion posterior to the hands specified in a cross-hands position across the chest of the infant: folding a protective portion of the vest device over and enclosing at least the anterior portion of the torso, hands and arms of the infant; and supplying a supportive force on the protective portion in the anterior direction of the folded and enclosed protective portion to provide a separation of the folded and enclosed protective portion away from the hands and arms while the hands are in a specified crossed-hands position on the torso, across the chest of the infant. Moreover, wherein the folded and enclosed protective portion prevents the arms and hands traveling beyond the enclosed protective portion thereby preventing any self-dislodgement by the infant of the medical life-sustaining supply lines or equipment. Further, wherein the separation of the folded and enclosed protective portion provides: clearance to allow the hands and arms to move in the posterior-anterior direction, lateral-medial direction, and superior-inferior direction relative to the chest of the torso. Further yet, wherein by allowing for the free movement and proper alignment of infant's arms and hands and which are allowed to touch one another, thereby not inhibiting the ability to explore and expand brain development through tactile stimulation and therefore fostering healthy neuronal pathways of the infant as the infant develops a sense of where it is in space and time as it continues to grow outside of the womb.

An aspect of an embodiment of the present invention provides, among other things, a protective vest device that will adequately secure an infant from the ability to self-dislodge medical life-sustaining (or non-life-sustaining) supply lines or equipment, while also supporting proper body alignment. The protective device mitigates self-dislodgement while allowing for free movement and proper alignment of infant's arms and hands and which are allowed to touch one another, thereby not inhibiting the ability to explore and expand brain development through tactile stimulation and therefore fostering healthy neuronal pathways of the infant. The fostering healthy neuronal pathways is provided by, for example, allowing the hands to touch one another as the infant develops a sense of where it is in space and time as it continues to grow outside of the womb. By maintaining proper body alignment of infant in the device and the configuration of the device, the device supports healthy musculoskeletal development with a stretchy womb like material to mimic the spring back effect of the uterine wall when a fetus pushes against a uterus.

An aspect of an embodiment of the present invention provides, among other things, midline alignment, which supports proper musculoskeletal formation in preterm infants.

An aspect of an embodiment of the present invention provides, among other things, optimal and healthy containment of the arms, and which prevents possible dislodgement of the endotracheal tube (ETT) and/or holding device, as infants move their arms upward toward the face (or other areas on the body of concern).

An aspect of an embodiment provides, among other things, a protective vest device (and related method) that will adequately secure an infant from the ability to self-dislodge medical life-sustaining supply lines or equipment, while also supporting proper body alignment. More particularly, while mitigating unplanned dislodgement, the protective device allows for free movement and proper alignment of infant's arms and hands and which are allowed to touch one another, thereby not inhibiting the ability to explore and expand brain development through tactile stimulation and therefore fostering healthy neuronal pathways of the infant. The fostering healthy neuronal pathways is provided by, for example, allowing the hands to touch one another as the infant develops a sense of where it is in space and time as it continues to grow outside of the womb. By maintaining proper body alignment of infant in the device and the configuration of the device, the device supports healthy musculoskeletal development with a stretchy womb-like material to mimic the spring back effect of the uterine wall when a fetus pushes against a uterus.

An aspect of an embodiment provides, among other things, a protective vest device including a lateral portion that provides body alignment (as, for example, it wraps around the torso of the infant). An aspect of an embodiment provides, among other things, a protective vest device including protective portion that provides the body alignment, as well as the alignment of the hands and arms (as, for example, as it encloses about and contains the torso, arms and hands of the infant in a dome-like or arch-like fashion). In an embodiment, by maintaining proper body alignment the device supports healthy musculoskeletal development with a stretchy womb-like material to mimic the spring back effect of the uterine wall when the fetus pushes against the uterus.

In an embodiment, the folded and enclosed protective portion of the protective vest device is configured (e.g., material structure, material consistency and contour/shape) to provide a stretchy womb-like simulated material to mimic the spring back effect of the uterine wall when a fetus pushes against a uterus.

An aspect of an embodiment provides a ventilator vest device for preventing a self-extubation of an endotracheal tube (ETT) by an infant while allowing free movement and proper alignment of an infant's hands and arms.

An aspect of an embodiment provides a protective vest device for preventing a self-dislodgement by an infant of medical life-sustaining supply lines or equipment while allowing free movement and proper alignment of an infant's hands and arms.

The present disclosure relates generally to ventilator vest device that will adequately secure an infant from the ability to self-extubate an endotracheal tube (ETT), while also supporting proper body, hands, and arms alignment. More particularly, while mitigating self-extubations) the ventilator device allows for free movement and proper alignment of infant's arms and hands and which are allowed to touch one another, thereby not inhibiting the ability to explore and expand brain development through tactile stimulation and therefore fostering healthy neuronal pathways of the infant. The fostering healthy neuronal pathways is provided by, for example, allowing the hands to touch one another as the infant develops a sense of where it is in space and time as it continues to grow outside of the womb.

An aspect of an embodiment of the present invention provides, optionally, swaddling of the infant, which fosters comfort.

Most often, intubated neonates are not sedated, which places them at increased risk for unplanned extubations (UE). An aspect of an embodiment of the present invention provides, among other things, a vest (and related method) that will help to enclose their arms and hands to prevent self-extubations (or other type of self-dislodgements of medical lines or equipment), while allowing proper developmental processes through mid-body alignment. In an embodiment, the midriff of the infant will remain uncovered, affording the opportunity for bedside nursing to properly manage umbilical lines.

Unplanned extubations (UEs) are the fourth leading adverse event in NICU's across America (See Merkel et al. [See 5], 2014: Panagos & Pearlman, 2017 [See 3]: Powell, Gilbert, & Volsko, 2016 [See 4]), and therefore it is important to adequately manage a neonate's airway.

Also, by providing a swaddling effect with the use an aspect of an embodiment of the present invention ventilator vest, it will not only contain their arms and hands, but also supply a form of natural soothing, and thus decreasing the need for sedation in vulnerable developing brains.

Neonatal intensive care units (NICUs) across America continue to experience the same rate of unplanned extubations (UEs) over the past 30 years [See 1]. The incidence of UEs lead to life-altering sequalae for our most vulnerable patient population. An aspect of an embodiment of the present invention provides, among other things, a product (and related method) to effectively reduce the rate of UEs across America (as well as reducing the self-dislodgement of other medical supply lines and equipment). With a growing trend amongst insurance carriers, including Medicare and Medicaid, to withhold payments based on patient outcomes, there is a strong indication for the need to reduce the rates of UEs. The market currently lacks any device which will adequately secure an infant from the ability to self-extubate, while also supporting proper body alignment.

An aspect of an embodiment of the present invention provides, among other things, a developmentally appropriate protective vest device (e.g., ventilator vest device), whereby the infant's hands will remain contained and enclosed, while allowing free movement and proper alignment of their arms. The protective portion provides an environment in which the arms and hands are allowed to touch one another, thereby not inhibiting the ability to explore and expand brain development through tactile stimulation. The swaddle element, which is an optional element of the vest, will provide a soothing effect, mimicking the womb, which will calm agitated infants, also decreasing the possibility for self-extubation. In an embodiment, simplified Velcro attachments (or other attachment mechanisms, materials, and means) will afford the bedside resident nurse (RN) the ability to easily perform hourly assessments of any intravenous (IV) sites on the arms, while the shortened nature of the vest will allow continuous visualization of any umbilical lines.

An aspect of an embodiment of the present invention provides, among other things, a protective vest device (e.g., ventilator vest device) that allows the hands of the infant to touch one another thereby fostering healthy neuronal pathways of the infant. The fostering healthy neuronal pathways is provided by, for example, allowing the hands to touch one another as the infant develops a sense of where it is in space and time as it continues to grow outside of the womb.

In an embodiment, the protective vest device, including but not limited thereto, the supine portion, lateral portion, and/or protective portion may be comprised of at least one or more of any combination of the following materials: polyester, spandex, rayon, or cotton (as well as other materials as desired or required). In an embodiment, the contour, structure and configuration of the protective vest device may be designed to provide a stretchy womb-like simulated material to mimic the spring back effect of the uterine wall when a fetus pushes against a uterus.

In an embodiment, the protective device is a continuous object, as a whole in a single piece. In an embodiment, the supine portion, lateral portion, and protective portion are (collectively) a continuous object, as a whole in a single piece. In an embodiment, the supine portion, lateral portion, protective portion, and support portion are (collectively) a continuous object, as a whole in a single piece. In an embodiment, all of the parts and components of the protective device are (collectively) a continuous object, as a whole in a single piece. By having a continuous object, as a whole in a single piece, the practitioner, nurse, doctor, or clinician can readily attend to the medical care and dressing of the infant without the need of obtaining and acquiring individual parts and pieces. For example, the protective device is readily available without needing add-ons, alterations, additional-items, and fixes. The continuous object provides consistency, and reduces time and effort. Moreover, the continuous object embodiment promotes an optimal, safe, and efficacious design to be regularly practiced, and with repeatability and ease of use. Alternatively, the various parts and components may be physically separated and assembled during the medical care and dressing of the infant.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The invention itself, together with further objects and attendant advantages, will best be understood by reference to the following detailed description, taken in conjunction with the accompanying drawings.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

Figure 1:
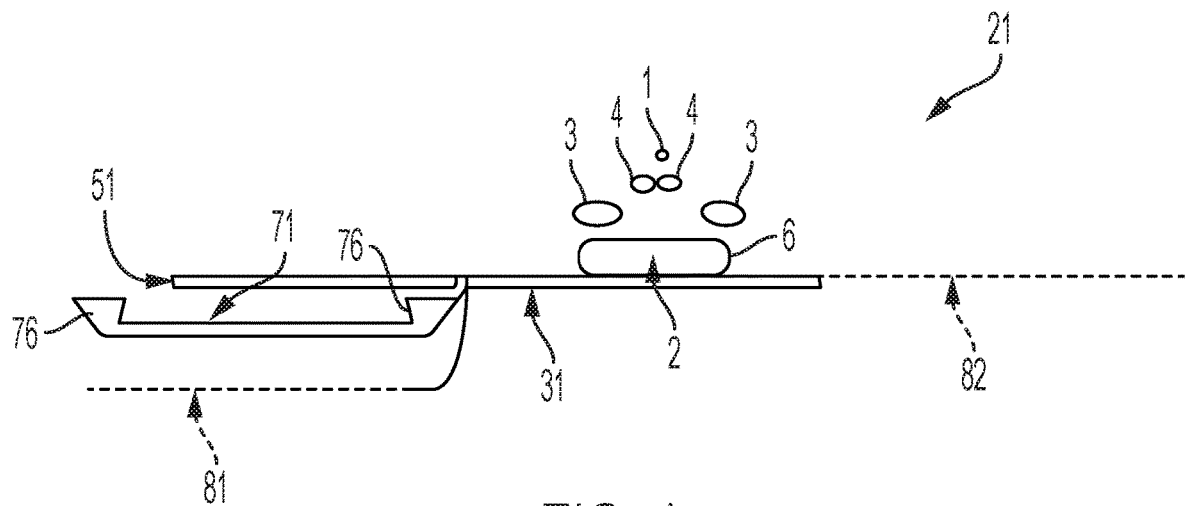
FIG. 1 provides a cross-sectional view (in the cranial direction) of an aspect of an embodiment of the protective vest device configured to receive the neonatal subject in the supine position including a lateral portion in an unwrapped position, for example and a protective portion in an unenclosed position, unfolded position or uncontained position.

FIG. 1 provides a cross-sectional view (in the cranial direction) of an aspect of an embodiment of the protective vest device 21 including a supine portion 31 configured to receive the neonatal subject 2 in the supine position illustrated with arms 3, hands 4, and torso 6. The ventilator vest device 21 further includes a lateral portion 51 (in an unwrapped position, for example) and a protective portion 71 (in an unenclosed position, unfolded position or uncontained position, example). The protective portion 71 is on the right side of the neonatal subject 2 (left side of the illustration). The protective portion 71 includes a support portion 76 at or proximal to its edges. The support portion 76 may be a portion of the protective portion 71 that includes pleats of the fabric or a material to provide greater rigidity, such as relative to the remaining portions of the protective portion 71. The support portion 76 may be a portion of the protective portion 71 that includes heavier fabric or material, stiffer fabric or material or thicker fabric or material compared to the rest of the protective portion 71. In an embodiment, the support portion 76 may provide frame members, strut members, spring, or structural members to provide adequate rigidity, support and direction to form the dome, umbrella-like shape, or arch, and thus the clearance and separation from the hands in the cross-hands position laying on the chest of the infant 2.

Figure 2:
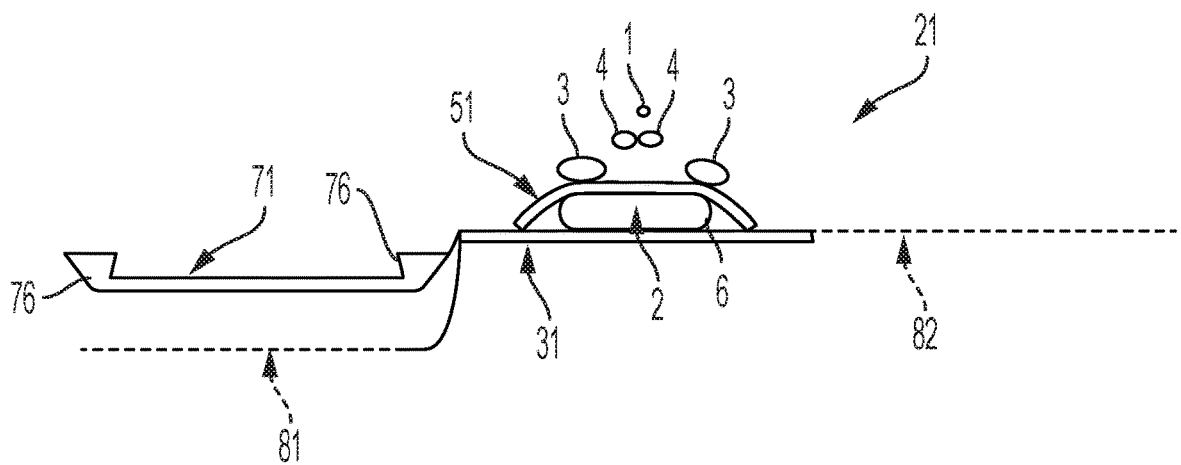
FIG. 2 provides a cross-sectional view (in the cranial direction) of an aspect of an embodiment of the protective vest device, as shown in FIG. 1 for example, whereby the device is now shown with the lateral portion in a wrapped position, FIG. 3 provides a cross-sectional view (in the cranial direction) of an aspect of an embodiment of the protective vest device, as shown in FIG. 2 for example, whereby the protective portion is configured to enclose around and contain the arms and hands while allowing specified body, arms and hands alignment, and specified clearance and movement of the arms and hands.

FIG. 2 provides a cross-sectional view (in the cranial direction) of an aspect of an embodiment of the protective vest device 21, as shown in FIG. 1 for example, whereby the device is now shown with the lateral portion 51 in a wrapped position, i.e. the lateral portion 51 is configured to wrap around the torso 6 underneath (posterior to) the arms 3 and hands 4 allowing the arms 3 and hands 4 to be free or unencumbered. The protective portion 71 remains in the unenclosed position, unfolded position, or uncontained position. As shown, the lateral portion 51 wraps around at least the anterior portion of the torso 6.

Figure 3:
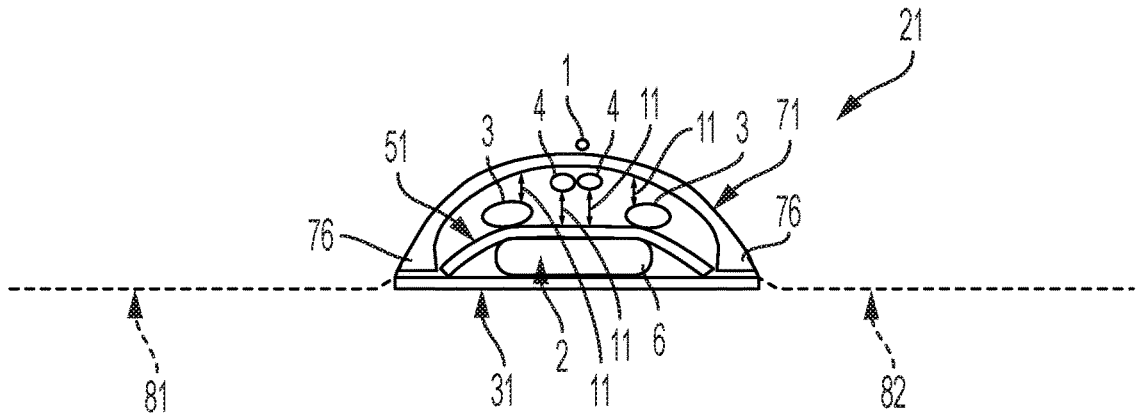
Figure 10:
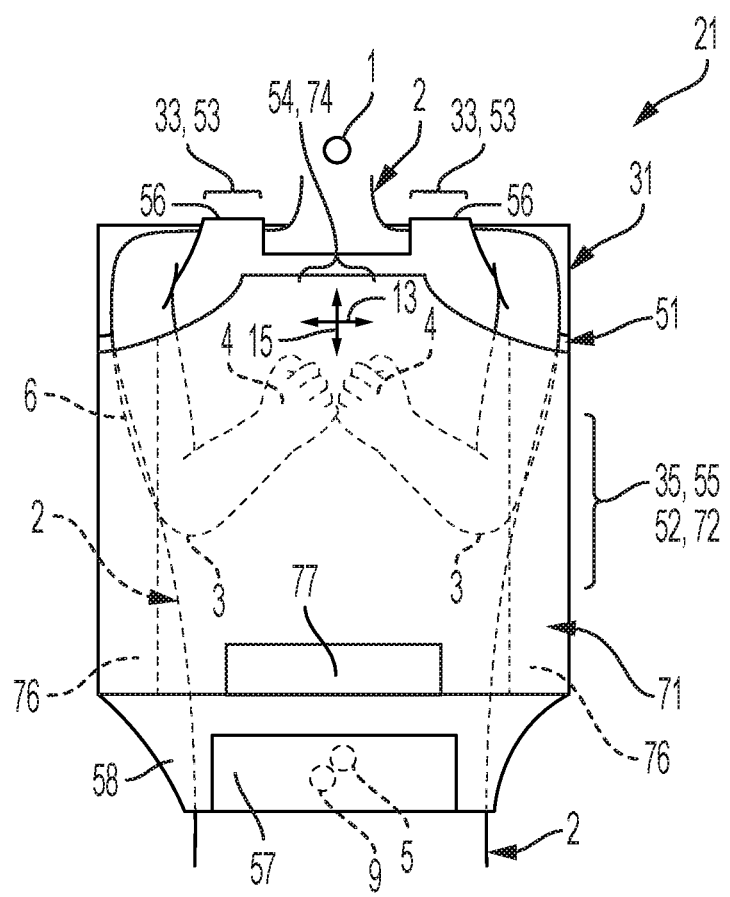
FIG. 10 provides a plan view (anterior view) of an aspect of an embodiment of the protective vest device, as shown in FIG. 9 for example, whereby the protective portion is configured to enclose around and contain the arms and hands while allowing specified body, arms and hands alignment, and specified clearance and movement of the arms and hands.
Figure 11:
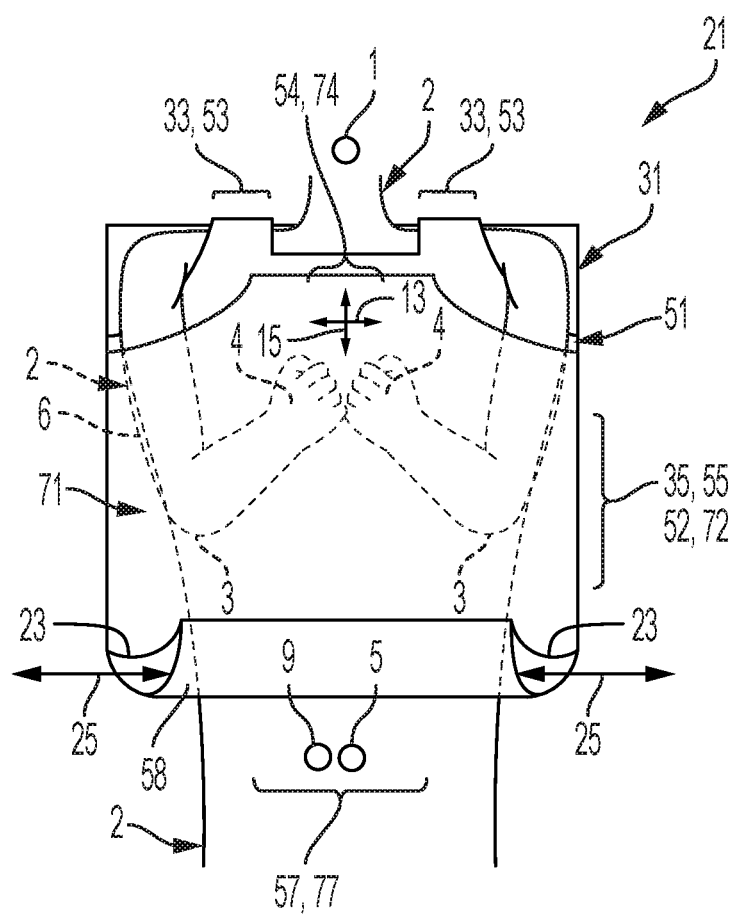
FIG. 11 provides a plan view (anterior view) of an aspect of an embodiment of the protective vest device, as shown in FIG. 10 for example, whereby the device is now shown with flap region of the lateral portion (which includes the lateral portion abdomen connector) is folded over protective portion, and therefore abdomen connector is now attached to protective portion abdomen connector of the protective portion.

FIG. 3 provides a cross-sectional view (in the cranial direction) of an aspect of an embodiment of the protective vest device 21, as shown in FIG. 2 for example, whereby the protective portion 71 is configured to enclose around and contain the arms 3 and hands 4 while allowing some posterior-anterior clearance and movement of the arms 3 and hands 4, illustrated by arrows, 11; and while allowing some lateral-medial movement of the arms 3 and hands 4, illustrated by arrow, 13 (shown in FIGS. 10 and 11, for example), and allowing superior-inferior clearance and movement of the arms 3 and hands 4, illustrated by 15 (shown in FIGS. 10 and 11, for example). The support portion 76 of the protective portion 71 assists in directing or supporting the protective portion 71 so as to provide a dome like, arch-like or umbrella-like shape over the neonatal subject 2 thereby achieving the clearance: posterior-anterior clearance and movement of the arms 3 and hands 4 (referenced as 11), lateral-medial movement of the arms 3 and hands 4 (referenced as 13 in FIGS. 10 and 11), and superior-inferior clearance and movement of the arms 3 and hands 4 (referenced as 15 in FIGS. 10 and 11). For example, the illustration is intended to represent the hands 4 and arms 3 while the hands 4 are in a specified crossed-hands position on the torso 6 (i.e., across the chest of the infant 2).

Still referring to FIG. 3 (as which shall be applicable to FIG. 6), the protective portion 71 in its enclosed and contained position prevents the infant 2 from self-dislodging the medical life-sustaining supply lines or equipment 1 and/or 9 (both references 1 and 9 are shown in FIGS. 7-13). For example in an application or embodiment, but not limited thereto, the protective vest device 21 may be a ventilator vest device 21 that prevents the infant 2 from self-extubating an endotracheal tube (ETT) 1.

In an embodiment, other types of medical life-sustaining supply lines or equipment that may possibly be dislodged (besides the self-extubating of an endotracheal tube (ETT) 1), which may include, but not limited thereto, the following: nasogastric tubes (NG tubes) 1, orogastric tubes (OG tubes) 1, bubble continuous positive airway pressure (bCPAP) tube/line 1, umbilical arterial catheter (UAC catheter) 9, umbilical venous catheter (UVC catheter) 9 (reference 9 shown in FIGS. 7-13).

In an embodiment, the medical life-sustaining supply lines or equipment 1 may be applied by a variety or nasogastric means or orogastric means.

In an embodiment, the medical life-sustaining supply lines or equipment 9 may be applied by a variety umbilical means.

In an embodiment, the medical life-sustaining supply lines or equipment may be applicable to other regions of the head (other than nasal and mouth), as well as to the upper limbs, lower limbs, neck, shoulder, lower torso, or other anatomical regions of the infant other than as designated (i.e., outside the confines of the vest 21).

In an embodiment, the related life-sustaining supply lines or equipment (designated as 1 or 9 or other anatomical regions of the infant) are not necessarily considered life-sustaining, but rather may be for maintenance, evaluation, diagnostic, analysis, or monitoring or medical purposes, etc.

Figure 4:
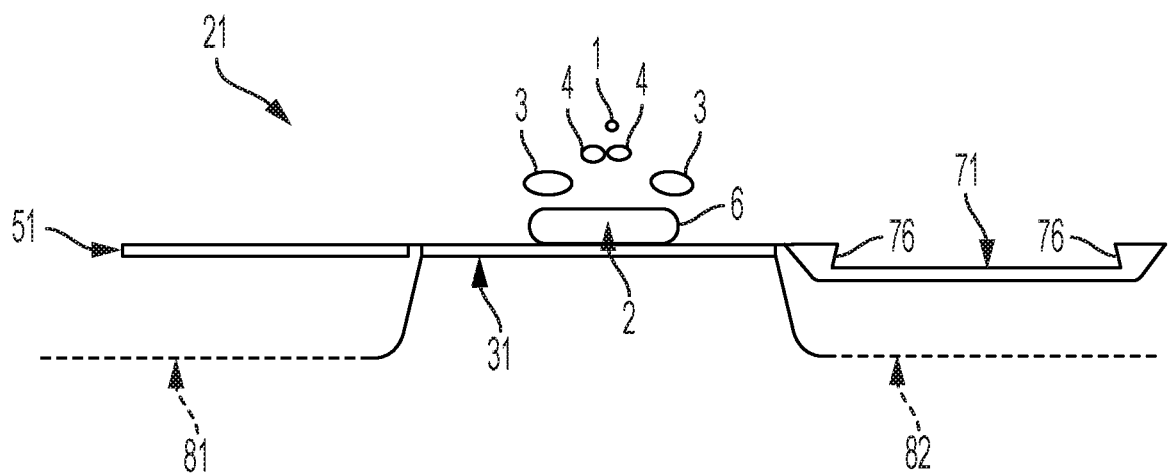
FIG. 4 provides a cross-sectional view (in the cranial direction) of an aspect of an embodiment of the protective vest device configured to receive the neonatal subject in the supine position including a lateral portion in an unwrapped position, for example and a protective portion in an unenclosed position, unfolded position or uncontained position.

FIG. 4 provides a cross-sectional view (in the cranial direction) of an aspect of an embodiment of the protective vest device 21, as similarly shown in FIG. 1, for example, except the protective portion 71 is on the left side of the neonatal subject 2 (right side of the illustration) rather than the right side of the neonatal subject 2.

Figure 5:
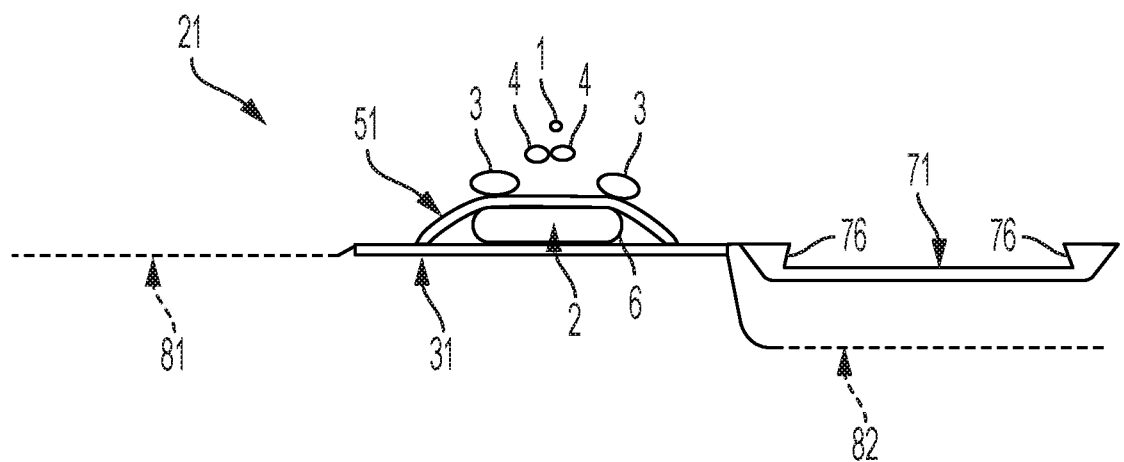
FIG. 5 provides a cross-sectional view (in the cranial direction) of an aspect of an embodiment of the protective vest device, as shown in FIG. 4 for example, whereby the device is now shown with the lateral portion in a wrapped position, FIG. 6 provides a cross-sectional view (in the cranial direction) of an aspect of an embodiment of the protective vest device, as shown in FIG. 5 for example, whereby the protective portion is configured to enclose around and contain the arms and hands while allowing specified body, arms and hands alignment, and specified clearance and movement of the arms and hands.

FIG. 5 provides a cross-sectional view (in the cranial direction) of an aspect of an embodiment of the protective vest device 21 with the lateral portion 51 in a wrapped position, as similarly shown in FIG. 2, for example, except the protective portion 71 is on the left side of the neonatal subject 2 (right side of the illustration) still in the unenclosed position, unfolded position, or uncontained position rather than the right side of the neonatal subject 2.

Figure 6:
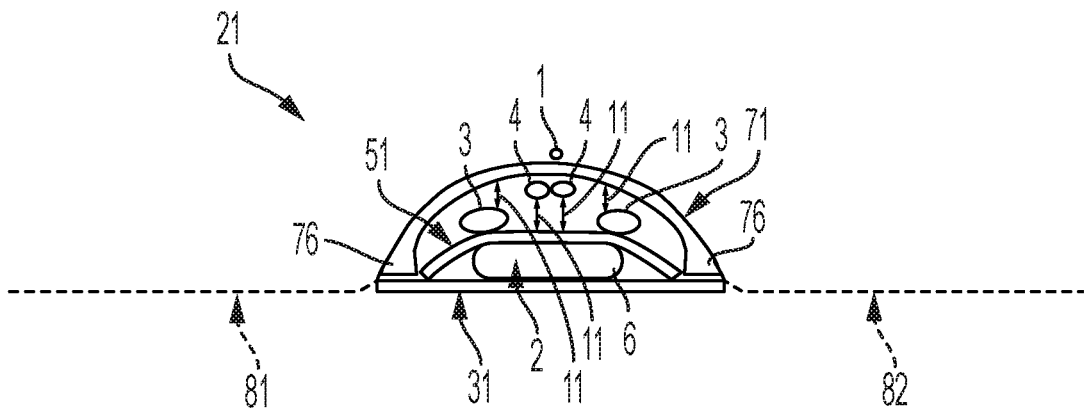

FIG. 6 provides a cross-sectional view (in the cranial direction) of an aspect of an embodiment of the protective vest device 21 with the protective portion 71 in an enclosed, folded or contained position, as similarly shown in FIG. 3, for example, except the protective portion 71 had originated from the left side of the neonatal subject 2 (right side of the illustration).

Still referring to FIGS. 1-6, in an embodiment, the protective vest device 21 may optionally include a first swaddle portion 81 and/or second swaddle portion 82 as shown with dashed lines while in an open (unwrapped position).

Sill referring to FIGS. 1-6, in an embodiment, any one or more of the supine portion 31, lateral portion 51, protective portion 71, support portion 76, and swaddle portions 81, 82 may be the same material, as a whole in a single piece, e.g., continuous object, as a whole in a single piece.

Any of the connectors referenced in FIGS. 1-13 may be a variety of connector types to effect the attachment, such as after a fold, such as including at least one or more of any combination of the following: Velcro, snaps, buttons, adhesive material, latches, couplings, fasteners, mounts, or hook and loops, as well as otherwise available connector types.

Any of the connectors referenced in FIGS. 1-13 may be illustrated as a single connector. However, it should be appreciated that more than one connector may be employed in instances where a single connector may be illustrated in the drawings.

Any of the connectors referenced in FIGS. 1-13 may be illustrated on a particular side of a component. However, it should be appreciated that a given connector may be employed on the opposite surface (other than as illustrated) provided that the surface (material) is flipped or folder over so as to be consistent with the teachings of the present disclosure.

Figure 7:
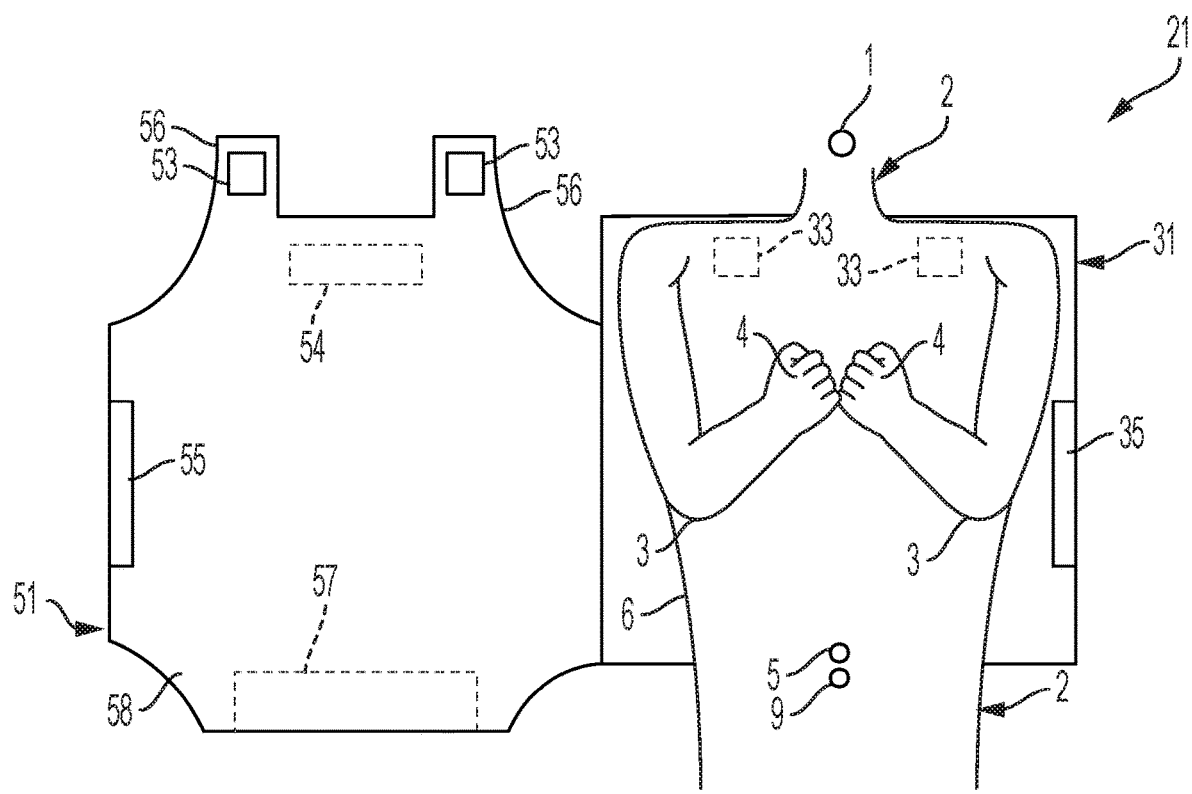
FIG. 7 provides a plan view (anterior view) of an aspect of an embodiment of the protective vest device configured to receive the neonatal subject in the supine position including a lateral portion in an unwrapped position, for example and a protective portion in an unenclosed position, unfolded position or uncontained position.

FIG. 7 provides a plan view (anterior view) of an aspect of an embodiment of the protective vest device 21 including a supine portion 31 configured to receive the neonatal subject 2 in the supine position illustrated with arms 3, hands 4, and torso 6. The protective vest device 21 further includes a lateral portion 51 (in an unwrapped position, for example, on the right side of the neonatal subject 2 (left side of the illustration)) and a protective portion 71 (which is not shown in an unenclosed position, unfolded position, or uncontained position, but may be understood to be located posterior to the lateral portion 51 for the time being). The supine portion 31 may have a supine portion shoulder connector 33. The supine portion shoulder connector 33 is illustrated with dashed lines being located on the posterior surface of the supine portion 33. The supine portion shoulder connector 33 may also be located on the anterior surface or cranial side of the supine portion 31. The lateral portion 51 may have lateral portion shoulder connector 53 on the cranial side of the lateral portion 51. In an embodiment, a shoulder strap-like feature 56 may be provided. Alternatively, the lateral portion shoulder connector 53 may be positioned on the posterior or anterior surface of the first layer 51.

Still referring to FIG. 7, the supine layer 33 may have a supine portion side body connector 35 along its edge. Also, the lateral portion 51 may have lateral portion side body connector 55 on the edge of the lateral portion 51. Still yet, the lateral portion 51 may have lateral portion abdomen connector 57, which is illustrated with dashed lines being located on opposite surface of the lateral portion 51 as can be viewed in the illustration (and which may also be disposed on a flap region 58 for implementation in a subsequent position, to be discussed later). Further, the lateral portion 51 may have lateral portion chest connector 54, which is illustrated with dashed lines being located on opposite surface of the lateral portion 51 as can be viewed in the illustration (which will be made available to connect with the protective portion 71 (not shown, and shall be discussed below).

Still referring to FIG. 7, it should be appreciated that in an embodiment, the lateral portion 51 could have been provided on the left side of the neonatal subject 2 (right side of the illustration) while still in the unwrapped position or unfolded position rather than the right side of the neonatal subject 2 (left side of the illustration) as currently shown in FIG. 7.

Figure 8:
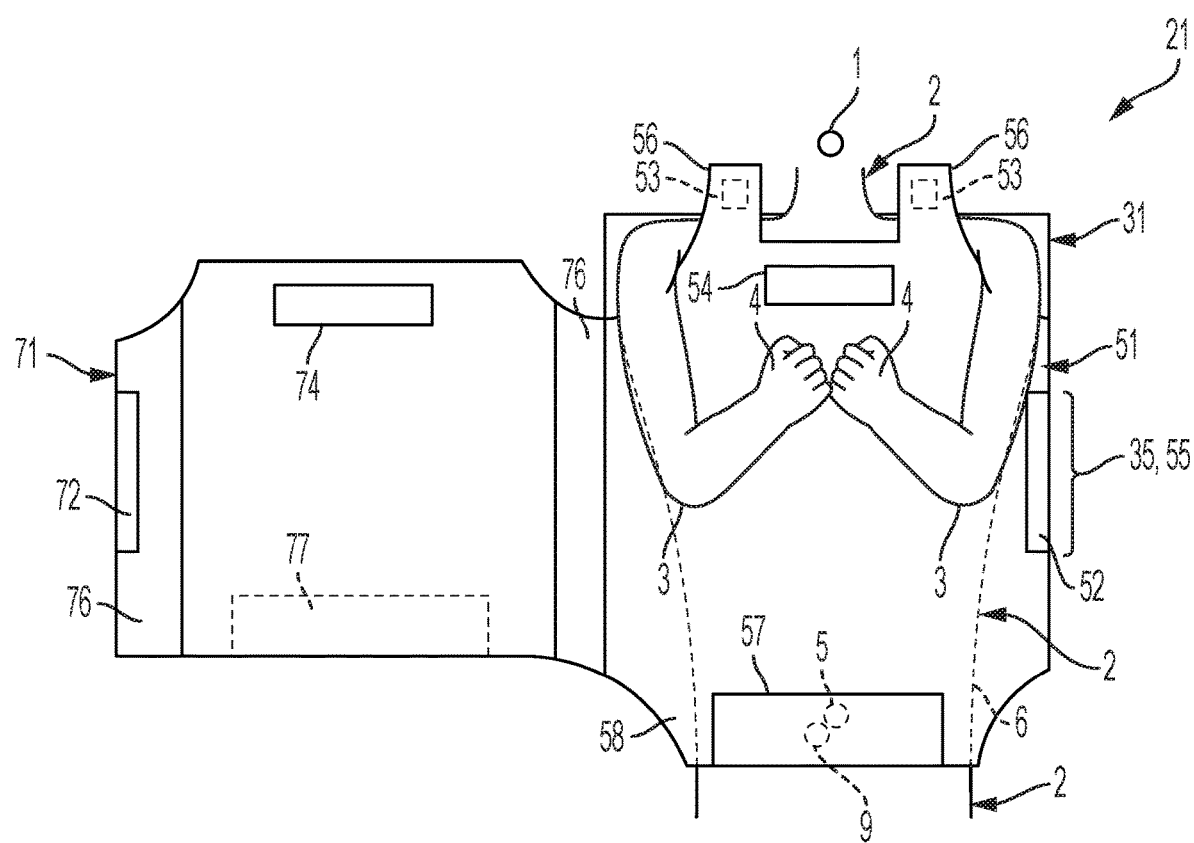
FIG. 8 provides a plan view (anterior view) of an aspect of an embodiment of the protective vest device, as shown in FIG. 7 for example, whereby the device is now shown with the lateral portion in a wrapped position.

FIG. 8 provides a plan view (anterior view) of an aspect of an embodiment of the protective vest device 21, as shown in FIG. 7 for example, whereby the device 21 is now shown with the lateral portion 51 in a wrapped position, i.e. the lateral portion 51 is configured to wrap around the torso 6 underneath (posterior to) the arms 3 and hands 4 allowing the arms 3 and hands 4 to be free or unencumbered, while in a cross-hands position resting across the chest of the torso 6, for example. The protective portion 71 remains in the unenclosed position, unfolded position or uncontained position. As the lateral portion 51 is in a wrapped positioned, the supine portion side body connector 35 is attached to the lateral portion side body connector 55 on the edge of the lateral portion 51 (which may not visible by the current view, but generally reflected in the area denoted by curly bracket 35/55) allowing the arms 3 and hands 4 to be free or unencumbered.

Still referring to FIG. 8, the lateral portion 51 may have a lateral portion side body connector 52 on the edge of the lateral portion 51, which may be provided to eventually receive and attach to protective portion side body connector 72 disposed on the edge of the protective portion 71 (which will be discussed below).

Still referring to FIG. 8, the protective portion 71 may have a protective portion abdomen connector 77, which is illustrated with dashed lines being located on opposite surface of the protective portion 71 as can be viewed in the illustration. Next, the protective portion 71 may have a protective portion chest connector 74 which will eventually matchup and attach to the lateral portion chest connector 54 on the lateral portion 51 (which will be discussed below).

Still referring to FIG. 8, it should be appreciated that in an embodiment, the protective portion 71 could have been provided on the left side of the neonatal subject 2 (right side of the illustration) while still in the unenclosed position, unfolded position, or uncontained position rather than the right side of the neonatal subject 2 (left side of the illustration) as currently shown in FIG. 8.

Figure 9:
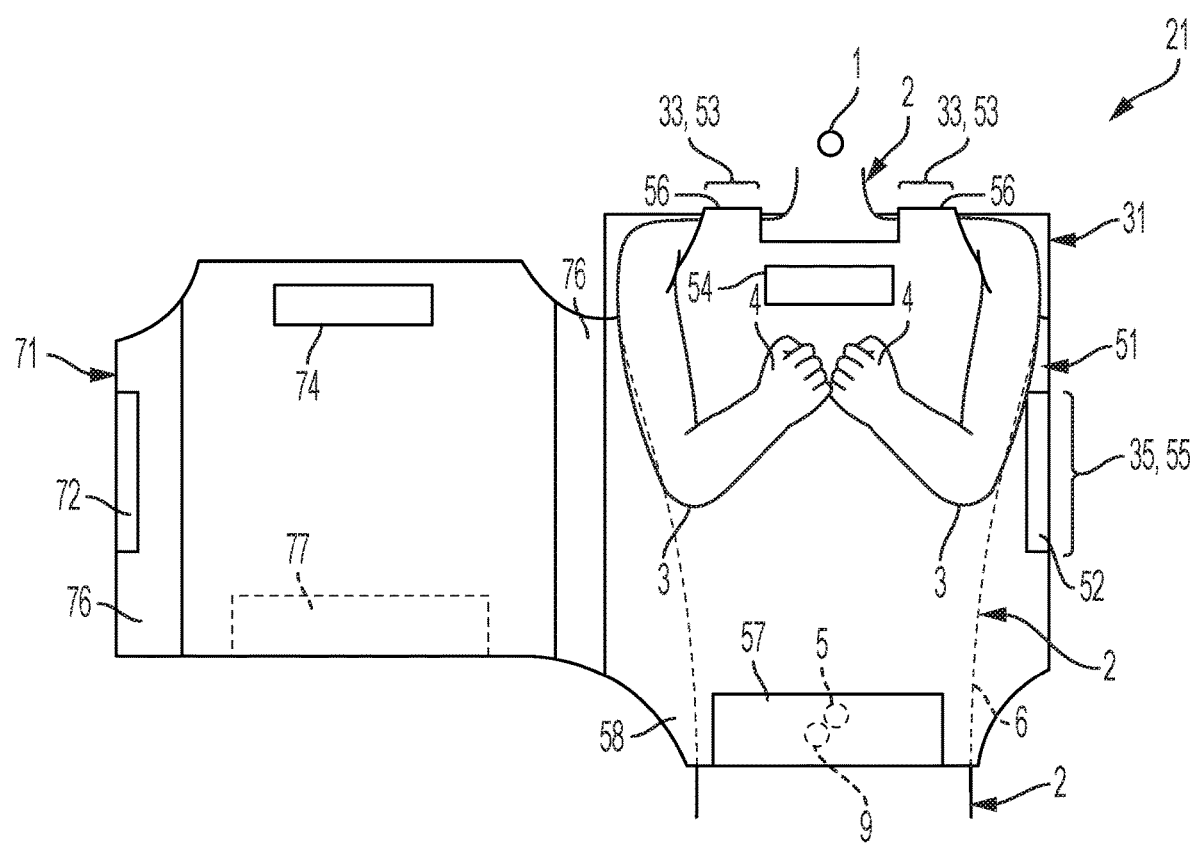
FIG. 9 provides a plan view (anterior view) of an aspect of an embodiment of the protective vest device 21, as shown in FIG. 8 for example, whereby the lateral portion shoulder connector 53 is now positioned around to the back shoulder of the subject 2 to attach to the supine portion connector 33.

FIG. 9 provides a plan view (anterior view) of an aspect of an embodiment of the protective vest device 21, as shown in FIG. 8 for example, whereby the lateral portion shoulder connector 53 is now positioned around to the back shoulder of the subject 2 to attach to the supine portion connector 33, which is located on the edge of the supine portion 31 (attachment is not visible by the current view, but generally reflected in the area denoted by curly bracket 33/53). As the lateral portion 51 is in a wrapped positioned about the torso 6, the lateral portion 51 allows the arms 3 and hands 4 to be free or unencumbered (yet still providing for proper torso (body) alignment). The lateral portion shoulder connector 53 may be disposed on the shoulder straps 56 or the general shoulder arear with said specific straps.

Still referring to FIG. 9, in an embodiment, there may be a plurality of supine portion side body connectors 35 and lateral portion side body connectors 55 running alongside the edge of the supine portion 31 and lateral portion 51 extending from the axilla of the subject 2 to the lower portion (abdomen side/end) of the supine portion 31 and lateral portion 51. In an embodiment, the supine portion side body connector 35 and lateral portion side body connector 55 may have extensive lengths to run alongside the edge of the supine portion 31 and lateral portion 51 extending from the axilla of the subject 2 to the lower region (abdomen side/end) of the supine portion 31 and lateral portion 51.

FIG. 10 provides a plan view (anterior view) of an aspect of an embodiment of the protective vest device 21, as shown in FIG. 9 for example, whereby the device 21 is now shown with the protective portion 71 in an enclosed position, folded position, or contained position, i.e. the protective portion 71 is configured to be folded and enclose around and contain the arms 3 and hands 4 while allowing arms 3 and hands 4 to touch one another, thereby not inhibiting the ability to explore and expand brain development through tactile stimulation and therefore fostering healthy neuronal pathways of the infant. The fostering healthy neuronal pathways is provided by, for example, allowing the hands to touch one another as the infant develops a sense of where it is in space and time as it continues to grow outside of the womb. In the position as illustrated, protective portion 71 is disposed over the lateral portion 51. The lateral portion side body connector 52 on the edge of the lateral portion 51 receives and attaches to the protective portion side body connector 72 (which may not visible by the current view, but generally reflected in the area denoted by curly bracket 52/72). Flap region 58 of the lateral portion 51 (which includes the lateral portion abdomen connector 57) is not yet folded over the protective portion 71, and therefore abdomen connector 57 is not yet attached to protective portion abdomen connector 77.

Still referring to FIG. 10, the support portion 76 of the protective portion 71 (which is illustrated by double dashed lines) assists in directing or supporting the protective portion 71 so as to provide a dome like, arch-like, or umbrella-like shape over the neonatal subject 2 (including hovering above and over the hands 4 and arms 3, so as to leave the hands 4 and arms 3 unencumbered, yet still providing for proper torso (body) 6, arms 3, and hands 4 alignment). In an alternate embodiment, the support portion 76 of the protective portion 71 may be provided on only one edge of the protective portion 71 if it is configured to sufficiently provide for the dome like, arch-like, or umbrella-like shape function over the neonatal subject 2 (including hovering above and over the hands 4 and arms 3, so as to leave the hands 4 and arms 3 unencumbered, yet still providing for proper torso (body) 6, arms 3, and hands 4 alignment). In an alternate embodiment, the support portion 76 of the protective portion 71 may be disposed on more than two generally opposing sides.

Still referring to FIG. 10 (as which shall be applicable to FIG. 11), the protective portion 71 in its enclosed and contained position prevents the infant 2 from self-dislodging the medical life-sustaining supply lines or equipment 1 and/or 9. For example in an application or embodiment, but not limited thereto, the protective vest device 21 may be a ventilator vest device 21 that prevents the infant 2 from self-extubating an endotracheal tube (ETT) 1, yet still providing for proper torso (body) 6, arms 3, and hands 4 alignment.

In an embodiment, other types of medical life-sustaining supply lines or equipment 1 that may be dislodged (besides the self-extubating of an endotracheal tube (ETT) 1), which may include, but not limited thereto, the following: nasogastric tubes (NG tubes) 1, orogastric tubes (OG tubes) 1, bubble continuous positive airway pressure (bCPAP) tube/line 1, umbilical arterial catheter (UAC catheter) 9, umbilical venous catheter (UVC catheter) 9.

In an embodiment, the medical life-sustaining supply lines or equipment 1 may be applied by a variety of nasogastric means or orogastric means.

In an embodiment, the medical life-sustaining supply lines or equipment 9 may be applied by a variety umbilical means.

In an embodiment, the medical life-sustaining supply lines or equipment 1 may be applicable to other regions of the head (other than nasal and mouth), as well as to the upper limbs, lower limbs, neck, shoulder, lower torso, or other anatomical regions of the infant 2 other than as designated (i.e., outside the confines of the vest 21).

In an embodiment, the related life-sustaining supply lines or equipment (designated as 1 or 9 or other anatomical regions of the infant) are not necessarily considered life-sustaining, but rather may be for maintenance, evaluation, diagnostic, analysis, or monitoring purposes, etc.

FIG. 11 provides a plan view (anterior view) of an aspect of an embodiment of the protective vest device 21, as shown in FIG. 10 for example, whereby the device 21 is now shown with the protective portion 71 in an enclosed position, folded position, or contained position, i.e. the protective portion 71 is configured to enclose around and contain the arms 3 and hands 4 while allowing arms 3 and hands 4 to touch one another, thereby not inhibiting the ability to explore and expand brain development through tactile stimulation (and yet still providing for proper torso (body) 6, arms 3, and hands 4 alignment). Moreover, in the position as illustrated, the flap region 58 of the lateral portion 51 (which includes the lateral portion abdomen connector 57) is folded over protective portion 71, and therefore abdomen connector 57 is now attached to protective portion abdomen connector 77 of the protective portion 71 (which may not visible by the current view; but generally reflected in the area denoted by curly bracket 57/77).

Still referring to FIG. 11, the protective portion 71 is configured to enclose around and contain the arms 3 and hands 4 while allowing some lateral-medial movement of the arms 3 and hands 4, illustrated by arrow, 13, and superior-inferior clearance and movement of the arms 3 and hands 4, illustrated by 15 (and posterior-anterior clearance and movement of the arms 3 and hands 4, illustrated by arrow, 11 (shown in FIGS. 3 and 6)). As the protective portion 71 is in an enclosed positioned, the protective portion abdomen connector 77 is attached to the lateral portion side abdomen connector 57 on the caudal side of the protective portion 71 allowing the arms 3 and hands 4 to be free or unencumbered.

Still referring to FIG. 11, the flap region 58 of the lateral portion 51 is folded over the protective portion 71 thereby providing or creating an opening, aperture or passage 23 about at the corner of the fold so as to allow or passage or traversal of medical devices or equipment through as reflected for example by the dashed line, 25. For example, the medical devices 25 or equipment to be passed through opening 23 may include an umbilical arterial catheter (UAC catheter), umbilical venous catheter (UVC catheter), peripherally inserted central catheter (PICC lines), peripheral intravenous catheter (PIV lines), or the like.

In an embodiment, the various components of the device 21 (such as, but not limited thereto supine portion 31, lateral portion 51, protective portion 71, support portion 76 and swaddle portion 81, 82) may only be as long as the length of the rib cage of the infant 2, so that any umbilical lines will be continuously visible by the medical team, including hourly depth affirmation performed by the bedside registered nurse (RN).

In an embodiment, the lateral portion 51 may be without a flap (such as referred to as 58) and therefore when the protective portion 71 is disposed over the lateral portion 51, then the protective portion abdomen connector 77 may be placed on and attach to the lateral portion abdomen connector 57 (without requiring a flap, and the folding of the flap).

Figure 12:
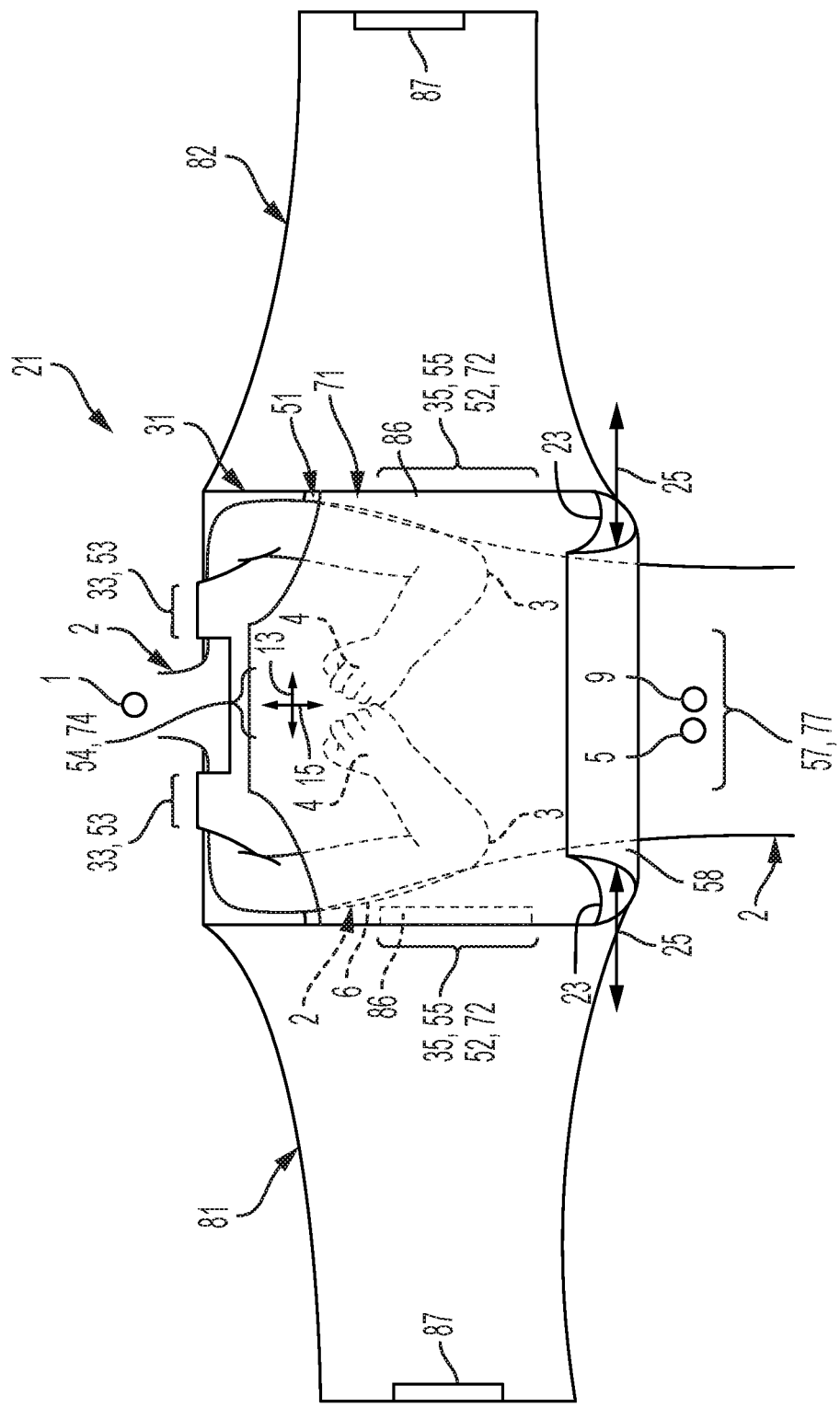
FIG. 12 provides a plan view (anterior view) of an aspect of an embodiment of the protective vest device, as shown in FIG. 11 for example, whereby the device is shown with an optional first swaddle portion, in an open position, and an optional second swaddle portion, in an open position.

FIG. 12 provides a plan view (anterior view) of an aspect of an embodiment of the protective vest device 21, as shown in FIG. 11 for example, whereby the device 21 is shown with an optional first swaddle portion 81, in an open position, having a first swaddle portion side body connector 86 (on the inner edge of the first swaddle portion 81 or along the edge of the posterior side of the device 21: of which is illustrated with dashed lines being located on opposite surface of the device 21 as can be viewed in the illustration) and first swaddle portion outer part connector 87 (at the outer edge). Similarly, in an embodiment, an optional second swaddle portion 82, in an open position, having a second swaddle portion side body connector 86 (on the inner edge of the second swaddle portion 82 or along the edge of the protective portion 71) and second swaddle portion outer part connector 87 (at the outer edge).

Figure 13:
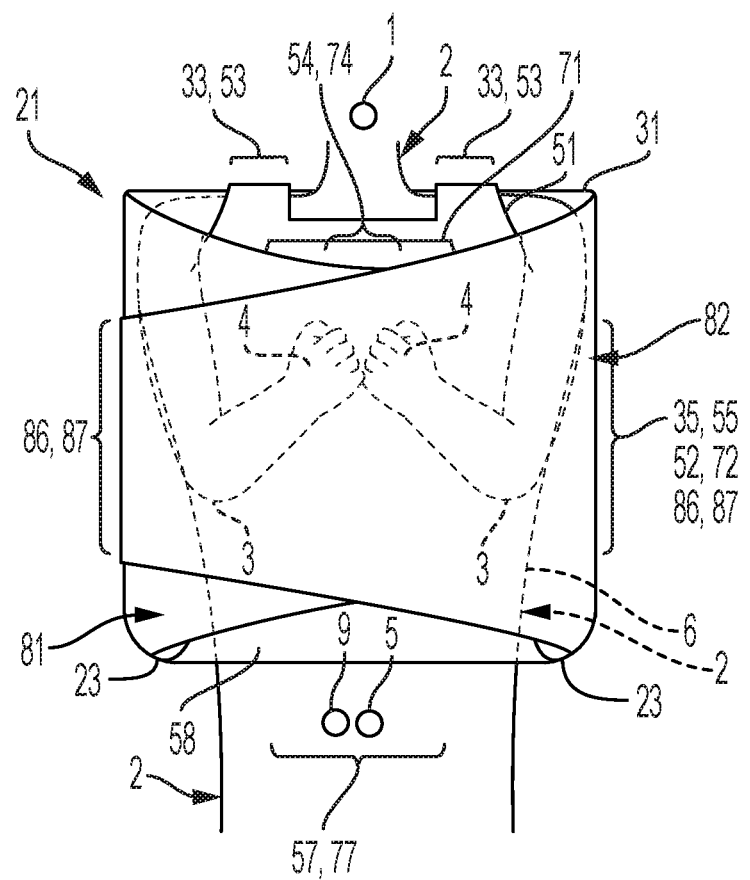
FIG. 13 provides a plan view (anterior view) of an aspect of an embodiment of the protective vest device, as shown in FIG. 12 for example, whereby the device is shown with the first swaddle portion and the second swaddle portion are configured to be folded over one another and to wrap around protective portion in its folded and wrapped position.

FIG. 13 provides a plan view (anterior view) of an aspect of an embodiment of the protective vest device 21, as shown in FIG. 12 for example, whereby the device 21 is shown with the first swaddle portion 81 and the second swaddle portion 82 are configured to be folded over one another and to wrap around protective portion 71 in its folded and wrapped position. With the optional first swaddle layer 81 and second swaddle layer 82, now in a wrapped position, each of their respective swaddle body side body connectors 86 are now attached to the opposing swaddle portion outer part connectors 87.

The swaddle element by wrapping one or both of the swaddle portions 81, which is a completely optional element of the vest device 21, will provide a soothing effect, mimicking the womb, which will calm agitated infants, also decreasing the possibility for self-extubation or self-dislodgement.

By providing a swaddling effect, as provided by one or both of the swaddle portions 81, 82, with the use of an embodiment of the present invention protective vest 21, it will not only contain the infant's arms 3 and hands 4, but also supply a form of natural soothing, and thus decreasing the need for sedation in vulnerable developing brains.

Still referring to FIG. 13, in an embodiment, employing one or both of the swaddle portions 81, 82, may employ a force against the dome-like, arch-like, or umbrella-like contour, shape, or configuration so as to press it inward (in the posterior direction). The swaddle portion are configured to apply force in the posterior direction to eliminate the separation (spacing) of said folded and enclosed protective position. As a result, the swaddle portions hold the infant in a more swaddled position, limiting arm movement as otherwise provided in other embodiments.

EXAMPLES

Practice of an aspect of an embodiment (or embodiments) of the invention will be still more fully understood from the following examples and experimental results, which are presented herein for illustration only and should not be construed as limiting the invention in any way.

Example and Experimental Results Set No. 1

The present inventor provides that current status of the industry is as follows: unplanned extubations (UPEs) are the fourth leading adverse event in American NICUs: UPEs cause intraventricular hemorrhage, ventilator-associated pneumonia, and chronic lung disease: UPE rates over the past 30 years remain the same; there is an association between agitation and UPE; and current swaddling techniques may have the potential to inhibit normal musculoskeletal development.

The present inventor submits the following: there is a need for an embodiment of the protective device to achieve the goal of preventing self-extubations (or self-dislodgements of other medical supply lines and equipment) in neonates; and an embodiment of the protective device invention provides a calming effect on neonates placed in the vest.

Example and Experimental Results Set No. 2

Market Potential

The business case for reducing UEs in the NICU environment is compelling, both for improving outcomes of the NICU patient (both short-term and long-term), as well as reducing the cost of the delivery of this care. The immediate cost reduction from reduced UEs would involve the elimination of medical staff time associated with treating the patient after the UE (including the time involved with reintubation procedures), as well as supply and imaging costs associated with the patient's care in this situation. However, if UEs can be reduced, far more significant cost avoidance would be realized in the areas of length of stay and the elimination of additional procedures required in the care of post UE NICU patients.

The challenge in the creation of a business case is the lack of recent research into the costs associated with care in the NICU environment, especially for those patients who have required assisted ventilation. While the use of endotracheal intubation is common in the NICU environment, statistics as to the number of patients per 100 requiring intubations are elusive. While dated, the currently available research provides the following support to the contention that significant cost reduction can be realized with the elimination of an UE:

In a 2003 study, the authors identified that UEs in a PICU environment led to patients experiencing a longer time on a ventilator than those who didn't experience an UE, and that this longer ventilator time exposed the patients to an increased risk of adverse effects associated with ventilator use. More significantly, they identified that the length of stay for patients that experienced an unplanned extubation doubled over those who did not.[7] [See 7]

"In the United States alone, 4 million babies are delivered annually, with almost 15 percent of those (500,000) being premature, defined as less than 37 weeks' gestational age. Daily NICU costs exceed $3,500 per infant, and it is not unusual for costs to top $1 million for a prolonged stay."[8] [See 8]

"Additionally, the United States has more than 400 pediatric ICUs, with approximately 4,044 beds, and more than 1,500 neonatal ICUs, with approximately 20,000 beds. Patients admitted to the neonatal ICU (NICU) are generally preterm with very low birth weight (i.e., less than 1500 grams [3.3 pounds]): these two conditions account for 70-90% of NICU admissions. Common to neonates are diagnoses of respiratory illnesses and infections. As with adults, mechanical ventilation is a common technological support in both pediatric and neonatal patients."[9] [See 9]

While the cost of NICU care delivery varies between hospitals, it is reasonable to forecast that reducing UEs can potentially eliminate tens of thousands of dollars per intubated patient, while more importantly improving their short and long-term health prospects.

For purposes of tentatively establishing the market potential for the Ventilator Vest, the following assumptions are made (using US market initially):

Half of the NICU's in the US perform intubation services, or approximately 750 NICUs could potentially use the Ventilator Vest.

Ventilator Vest will be used as a single-use item, requiring no laundering.

It is estimated that each NICU will maintain an inventory of fifty (50) items in each of three (3) sizes, for a total of 150 units per hospital/year.

ADDITIONAL EXAMPLES

Example 1. A protective vest device for preventing a self-dislodgement by an infant of medical life-sustaining supply lines or equipment while allowing free movement and proper alignment of an infant's hands and arms, the device comprising:

a supine portion for receiving the torso of the infant in a supine position:

a lateral portion, wherein the lateral portion is configured to fold over the torso of the infant without covering the hands and arms of infant to wrap around at least the anterior portion of the torso, and disposed posterior to the hands specified in a cross-hands position across the chest of the infant:

a protective portion including a support portion, wherein the protective portion is configured to fold over and enclose at least the anterior portion of the torso, hands and arms of the infant, and wherein the support portion provides supportive force in the anterior direction of the folded and enclosed protective portion to provide separation of the folded and enclosed protective portion away from the hands and arms while the hands are in a specified crossed-hands position on the torso, across the chest of the infant:

the separation of the folded and enclosed protective portion provides clearance to allow the hands and arms to move in the posterior-anterior direction, lateral-medial direction, and superior-inferior direction relative to the chest of the torso; wherein:

by allowing for the free movement and proper alignment of infant's arms and hands and which are allowed to touch one another, thereby not inhibiting the ability to explore and expand brain development through tactile stimulation and therefore fostering healthy neuronal pathways of the infant as the infant develops a sense of where it is in space and time as it continues to grow outside of the womb; and the folded and enclosed protective portion prevents the arms and hands traveling beyond the enclosed protective portion thereby preventing any self-dislodgement by the infant of the medical life-sustaining supply lines or equipment.

Example 2. The device of example 1, wherein the support portion is disposed on each generally opposing edges of the protective portion.

Example 3. The device of example 1 (as well as subject matter in whole or in part of example 2), wherein the folded and enclosed protective portion is configured to provide a stretchy womb-like simulated material to mimic the spring back effect of the uterine wall when a fetus pushes against a uterus.

Example 4. The device of example 1 (as well as subject matter of one or more of any combination of examples 2-3, in whole or in part), wherein the supine portion, lateral portion, and/or protective portion are comprised of at least one or more of any combination of the following materials: polyester, spandex, rayon, or cotton.

Example 5. The device of example 1 (as well as subject matter of one or more of any combination of examples 2-4, in whole or in part), wherein the support portion comprises at least one of any combination of the following:

pleated material, thicker-cross section of material relative to the remaining area of the protective portion, structural members, material having greater rigidity relative to the remaining area of the protective portion, frame members, or strut members.

Example 6. The device of example 1 (as well as subject matter of one or more of any combination of examples 2-5, in whole or in part), wherein the device is a continuous object, as a whole in a single piece.

Example 7. The device of example 1 (as well as subject matter of one or more of any combination of examples 2-6, in whole or in part), wherein the supine portion, lateral portion, and protective portion are a continuous object collectively, as a whole in a single piece.

Example 8. The device of example 1 (as well as subject matter of one or more of any combination of examples 2-7, in whole or in part), wherein the supine portion, lateral portion, protective portion, and support portion are a continuous object collectively, as a whole in a single piece.

Example 9. The device of example 1 (as well as subject matter of one or more of any combination of examples 2-8, in whole or in part), further comprising:
a first swaddle portion and a second swaddle portion, wherein the first swaddle portion and the second swaddle portion are configured to fold over one another and to wrap around the protective portion in its folded and enclosed position.

Example 10. The device of example 9 (as well as subject matter of one or more of any combination of examples 1-8, in whole or in part), wherein the wrapped first swaddle portion and the second swaddle portion are configured to apply force in the posterior direction to eliminate the separation of the folded and enclosed protective position.

Example 11. The device of example 1 (as well as subject matter of one or more of any combination of examples 2-10, in whole or in part), further comprising:
a first swaddle portion, wherein the first swaddle portion is configured to fold over and to wrap around the protective portion in its folded and enclosed position.

Example 12. The device of example 11 (as well as subject matter of one or more of any combination of examples 1-10, in whole or in part), wherein the wrapped first swaddle portion is configured to apply force in the posterior direction to eliminate the separation of the folded and enclosed protective position.

Example 13. The device of example 1 (as well as subject matter of one or more of any combination of examples 2-12, in whole or in part), wherein the medical life-sustaining supply lines or equipment includes at least one or more of the following types: nasogastric, orogastric, or umbilical.

Example 14. A method for preventing a self-dislodgement by an infant of medical life-sustaining supply lines or equipment while allowing free movement and proper alignment of an infant's hands and arms, the method comprising:
receiving the torso of the infant in a supine position on a supine portion of a vest device:
folding a lateral portion of the vest device over the torso of the infant without covering the hands and arms of infant to wrap around at least the anterior portion of the torso, and disposing the lateral portion posterior to the hands specified in a cross-hands position across the chest of the infant:
folding a protective portion of the vest device over and enclosing at least the anterior portion of the torso, hands and arms of the infant; and
supplying a supportive force on the protective portion in the anterior direction of the folded and enclosed protective portion to provide a separation of the folded and enclosed protective portion away from the hands and arms while the hands are in a specified crossed-hands position on the torso, across the chest of the infant:
wherein the folded and enclosed protective portion prevents the arms and hands traveling beyond the enclosed protective portion thereby preventing any self-dislodgement by the infant of the medical life-sustaining supply lines or equipment; and
wherein the separation of the folded and enclosed protective portion provides:
clearance to allow the hands and arms to move in the posterior-anterior direction, lateral-medial direction, and superior-inferior direction relative to the chest of the torso, wherein:
by allowing for the free movement and proper alignment of infant's arms and hands and which are allowed to touch one another, thereby not inhibiting the ability to explore and expand brain development through tactile stimulation and therefore fostering healthy neuronal pathways of the infant as the infant develops a sense of where it is in space and time as it continues to grow outside of the womb.

Example 15. The method of example 14, wherein the supine portion, lateral portion, and protective portion are provided as a continuous object collectively, as a whole in a single piece.

Example 16. The method of example 14 (as well as subject matter in whole or in part of example 15), wherein the supportive force is provided by a support portion of the protective portion.

Example 17. The method of example 16 (as well as subject matter of one or more of any combination of examples 14-15, in whole or in part), wherein the supine portion, lateral portion, protective portion, and support portion are provided as a continuous object collectively, as a whole in a single piece.

Example 18. The method of example 14 (as well as subject matter of one or more of any combination of examples 15-17, in whole or in part), wherein the folded and enclosed protective portion is configured to provide a stretchy womb-like simulated material to mimic the spring back effect of the uterine wall when a fetus pushes against a uterus.

Example 19. The method of example 14 (as well as subject matter of one or more of any combination of examples 15-18, in whole or in part), further comprising:
folding a first swaddle portion and a second swaddle portion over one another and to wrap around the protective portion in its folded and enclosed position.

Example 20. The method of example 19 (as well as subject matter of one or more of any combination of examples 15-18, in whole or in part), wherein the wrapped first swaddle portion and the second swaddle portion supplying a force in the posterior direction to eliminate the separation of the folded and enclosed protective position.

Example 21. The method of example 14 (as well as subject matter of one or more of any combination of examples 15-20, in whole or in part), further comprising:
folding a first swaddle portion over and to wrap around the protective portion in its folded and enclosed position.

Example 22. The method of example 21 (as well as subject matter of one or more of any combination of examples 15-20, in whole or in part), wherein the wrapped first swaddle portion is configured to apply force in the posterior direction to eliminate the separation of the folded and enclosed protective position.

Example 23. The device of example 14 (as well as subject matter of one or more of any combination of examples 15-22, in whole or in part), wherein the medical life-sustaining supply lines or equipment includes at least one or more of the following types: nasogastric, orogastric, or umbilical.

Example 24. The method of using any of the devices or their components or sub-components provided in any one or more of examples 1-13, in whole or in part.

Example 25. The method of manufacturing any of the devices or their components or sub-components provided in any one or more of examples 1-13, in whole or in part.

Example 26. The method of providing instructions (in written format, computer readable medium format, machine executable instructions format) of using any of the devices or their components or sub-components provided in any one or more of examples 1-13, in whole or in part.

Example 27. The method of providing instructions (in written format, computer readable medium format, or machine executable instructions format) of implementing the steps provided in any one or more of examples 13-23, in whole or in part.

REFERENCES

The devices, systems, apparatuses, compositions, materials and methods of various embodiments of the invention disclosed herein may utilize aspects (devices, systems, apparatuses, compositions, materials and methods) disclosed in the following references, applications, publications and patents and which are hereby incorporated by reference herein in their entirety, and which are not admitted to be prior art with respect to the present invention by inclusion in this section:

1. Silva P S, Reis M E, Aguiar V E, Fonseca M C. Unplanned extubation in the neonatal ICU: A systematic review, critical appraisal, and evidence-based recommendations. Respir Care. 2013: 58 (7): 1237-1245. doi: 10.4187/respcare.02164.
2. Dalgleish S, Kostecky L, Charania I. Special considerations in neonatal mechanical ventilation. Crit Care Nurs Clin North Am. 2016: 28 (4): 477-498. doi: S0899-5885(16) 30056-9.
3. Panagos P G, Pearlman S A. Creating a highly reliable neonatal intensive care unit through safer systems of care. Clin Perinatol. 2017: 44 (3): 645-662.
4. Powell B M, Gilbert E, Volsko T A. Reducing unplanned extubations in the NICU using lean methodology. Respir Care. 2016; 61 (12): 1567-1572. doi: respcare.04540.
5. Merkel L, Beers K, Lewis M M, Stauffer J, Mujsce D J, Kresch M J. Reducing unplanned extubations in the NICU. Pediatrics. 2014; 133 (5): 1367-72. doi: 10.1542/peds.2013-3334.
6. Barber J A. Unplanned extubation in the NICU. Journal of Obstetric, Gynecologic, & Neonatal Nursing. 2013: 42 (2): 233-238.
7. Kurachek S C, Newth C J, Quasney M W, et al. Extubation failure in pediatric intensive care: A multiple-center study of risk factors and outcomes. Crit Care Med. 2003: 31 (11): 2657-2664.
8. Muraskas J, Parsi K. The cost of saving the tiniest lives: NICUs versus prevention. Virtual Mentor. 2008; 10 (10): 655.
9. Critical care statistics. http://www.sccm.org/Communications/Pages/CriticalCareStats.aspx.
10. U.S. Pat. No. 8,782,831 B2, Houston, et al., "Baby Swaddle", Jul. 22, 2014.
11. U.S. Pat. No. 7,882,570 B2, Krier, J., "Infant Garment", Feb. 8, 2011.
12. U.S. Pat. No. 9,332,791 B2, Bush, et al., "Multipurpose Positioning Device for Infants", May 10, 2016.
13. Hatch, L. D., Grubb, P. H., Markham, M. H., Scott, T. A., Walsh, W. F., Slaughter, J. C., Ely, E. W. (2017). Effect of anatomical and developmental factors on the risk of unplanned extubation in critically ill newborns. American Journal of Perinatology, 34 (12), 1234-1240.
14. Ndakor, S. M., Nelson, M., & Pinheiro, J. (2017). Counting unplanned extubations: Marked variation among neonatologists. Journal of Perinatology, 37 (6), 698.

Moreover, for example, any of the methods of manufacturing the devices or items (or portions thereof) or as disclosed in the references, applications, publications and patents as disclosed in the above references (nos. 1-14), as well as techniques of manufacturing available to one skilled in the art are also incorporated by reference and may therefore be considered as part of the present invention and employed within the context of the invention (and which are not admitted to be prior art with respect to the present invention by inclusion in this section).

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A protective vest device for preventing a self-dislodgement by an infant of medical life-sustaining supply lines or equipment while allowing free movement and proper alignment of an infant's hands and arms, said device comprising:
    a supine portion for receiving the torso of the infant in a supine position;
    a lateral portion, wherein said lateral portion is configured to fold over the torso of the infant without covering the hands and arms of infant to wrap around at least the anterior portion of the torso, and disposed posterior to the hands specified in a cross-hands position across the chest of the infant;
    a protective portion including a support portion, wherein said protective portion is configured to fold over and enclose at least the anterior portion of the torso, hands and arms of the infant, and wherein said support portion provides supportive force in the anterior direction of the folded and enclosed protective portion to provide separation of the folded and enclosed protective portion away from the hands and arms while the hands are in a specified crossed-hands position on the torso, across the chest of the infant;
    said separation of said folded and enclosed protective portion provides clearance to allow the hands and arms to move in the posterior-anterior direction, lateral-medial direction, and superior-inferior direction relative to the chest of the torso; wherein:
        by allowing for the free movement and proper alignment of infant's arms and hands and which are allowed to touch one another, thereby not inhibiting the ability to explore and expand brain development through tactile stimulation and therefore fostering healthy neuronal pathways of the infant as the infant develops a sense of where it is in space and time as it continues to grow outside of the womb; and
    said folded and enclosed protective portion prevents the arms and hands traveling beyond the enclosed protective portion thereby preventing any self-dislodgement by the infant of the medical life-sustaining supply lines or equipment.

2. The device of claim 1, wherein said support portion is disposed on each generally opposing edges of said protective portion.

3. The device of claim 1, wherein said folded and enclosed protective portion is configured to provide a stretchy womb-like simulated material to mimic the spring back effect of the uterine wall when a fetus pushes against a uterus.

4. The device of claim 1, wherein said supine portion, lateral portion, and/or protective portion are comprised of at least one or more of any combination of the following materials: polyester, spandex, rayon, or cotton.

5. The device of claim 1, wherein said support portion comprises at least one of any combination of the following:
    pleated material, thicker-cross section of material relative to the remaining area of the protective portion, structural members, material having greater rigidity relative to the remaining area of the protective portion, frame members, or strut members.

6. The device of claim 1, wherein said device is a continuous object, as a whole in a single piece.

7. The device of claim 1, wherein said supine portion, lateral portion, and protective portion are a continuous object collectively, as a whole in a single piece.

8. The device of claim 1, wherein said supine portion, lateral portion, protective portion, and support portion are a continuous object collectively, as a whole in a single piece.

9. The device of claim 1, further comprising:
    a first swaddle portion and a second swaddle portion, wherein said first swaddle portion and said second swaddle portion are configured to fold over one another and to wrap around said protective portion in its folded and enclosed position.

10. The device of claim 9, wherein said wrapped first swaddle portion and said second swaddle portion are configured to apply force in the posterior direction to eliminate said separation of said folded and enclosed protective position.

11. The device of claim 1, further comprising:
    a first swaddle portion, wherein said first swaddle portion is configured to fold over and to wrap around said protective portion in its folded and enclosed position.

12. The device of claim 11, wherein said wrapped first swaddle portion is configured to apply force in the posterior direction to eliminate said separation of said folded and enclosed protective position.

13. The device of claim 1, wherein said medical life-sustaining supply lines or equipment includes at least one or more of the following types: nasogastric, orogastric, or umbilical.

14. A method for preventing a self-dislodgement by an infant of medical life-sustaining supply lines or equipment while allowing free movement and proper alignment of an infant's hands and arms, said method comprising:
    receiving the torso of the infant in a supine position on a supine portion of a vest device;
    folding a lateral portion of the vest device over the torso of the infant without covering the hands and arms of infant to wrap around at least the anterior portion of the torso, and disposing said lateral portion posterior to the hands specified in a cross-hands position across the chest of the infant;

folding a protective portion of the vest device over and enclosing at least the anterior portion of the torso, hands and arms of the infant; and supplying a supportive force on said protective portion in the anterior direction of the folded and enclosed protective portion to provide a separation of the folded and enclosed protective portion away from the hands and arms while the hands are in a specified crossed-hands position on the torso, across the chest of the infant;

wherein said folded and enclosed protective portion prevents the arms and hands traveling beyond the enclosed protective portion thereby preventing any self-dislodgement by the infant of the medical life-sustaining supply lines or equipment; and wherein said separation of said folded and enclosed protective portion provides:

clearance to allow the hands and arms to move in the posterior-anterior direction, lateral-medial direction, and superior-inferior direction relative to the chest of the torso, wherein:

by allowing for the free movement and proper alignment of infant's arms and hands and which are allowed to touch one another, thereby not inhibiting the ability to explore and expand brain development through tactile stimulation and therefore fostering healthy neuronal pathways of the infant as the infant develops a sense of where it is in space and time as it continues to grow outside of the womb.

15. The method of claim 14, wherein said supine portion, lateral portion, and protective portion are provided as a continuous object collectively, as a whole in a single piece.

16. The method of claim 14, wherein said supportive force is provided by a support portion of said protective portion.

17. The method of claim 16, wherein said supine portion, lateral portion, protective portion, and support portion are provided as a continuous object collectively, as a whole in a single piece.

18. The method of claim 14, wherein said folded and enclosed protective portion is configured to provide a stretchy womb-like simulated material to mimic the spring back effect of the uterine wall when a fetus pushes against a uterus.

19. The method of claim 14, further comprising:
folding a first swaddle portion and a second swaddle portion over one another and to wrap around said protective portion in its folded and enclosed position.

20. The method of claim 19, wherein said wrapped first swaddle portion and said second swaddle portion supplying a force in the posterior direction to eliminate said separation of said folded and enclosed protective position.

21. The method of claim 14, further comprising:
folding a first swaddle portion over and to wrap around said protective portion in its folded and enclosed position.

22. The method of claim 21, wherein said wrapped first swaddle portion is configured to apply force in the posterior direction to eliminate said separation of said folded and enclosed protective position.

23. The method of claim 14, wherein said medical life-sustaining supply lines or equipment includes at least one or more of the following types: nasogastric, orogastric, or umbilical.

* * * * *